United States Patent [19]

Gravelle

[11] Patent Number: 4,684,493
[45] Date of Patent: Aug. 4, 1987

[54] METHOD AND DEVICE FOR DETECTING DEFECTIVE NUCLEAR FUEL ELEMENTS

[75] Inventor: Alain Gravelle, Plessis Robinson, France

[73] Assignee: FRAGEMA, Paris, France

[21] Appl. No.: 562,057

[22] Filed: Dec. 16, 1983

[51] Int. Cl.⁴ .......................................... G21C 17/00
[52] U.S. Cl. .................................................. 376/252
[58] Field of Search ........................................ 376/252

[56] References Cited

U.S. PATENT DOCUMENTS

| | | | |
|---|---|---|---|
| 3,936,348 | 2/1976 | Wachter et al. | 376/252 |
| 3,945,245 | 3/1976 | Stehle et al. | 376/252 |
| 4,366,711 | 1/1983 | Weilbacher et al. | 376/252 |
| 4,517,152 | 4/1985 | Pieper et al. | 376/252 |

FOREIGN PATENT DOCUMENTS

| | | | |
|---|---|---|---|
| 2358658 | 10/1978 | France | |
| 2538155 | 6/1984 | France | 376/252 |

Primary Examiner—Salvatore Cangialosi
Attorney, Agent, or Firm—Pollock, Vande Sande & Priddy

[57] ABSTRACT

Defective fuel elements in an assembly immersed in a liquid are detected using ultrasonic absorption. A train of ultrasonic waves having a frequency and duration such that propagation takes place as Lamb waves is applied to an end portion of the sheath. The echoes are detected. Transmission and detection are repeated for different frequencies. Some frequencies are in a range corresponding to absorption by water which may be contained in the sheath. Other frequencies correspond to a range for which there is an echo at a mechanical defect of the sheath, such as a crack.

8 Claims, 15 Drawing Figures

METHOD AND DEVICE FOR DETECTING DEFECTIVE NUCLEAR FUEL ELEMENTS

BACKGROUND AND SUMMARY OF THE INVENTION

The invention relates to detection of defective nuclear fuel elements in an immersed assembly, the elements comprising a tubular metal sleeve closed by impervious caps, containing a stack of pellets of nuclear fuel surrounded by an atmosphere of gas under pressure. An especially important application of the invention is detection and identification of defective fuel elements in an assembly for a nuclear reactor, having a length of several meters, each containing a stack of fuel pellets held in contact by a spring compressed between the stack and an end cap and placed in a plenum occupied by the gas under pressure.

Various methods have already been used for determining whether a spent fuel assembly contains defective elements in which the sleeve is no longer gas tight. The most commonly used approach consists of placing the irradiated assembly removed from the nuclear reactor in a cell where it is heated, so that the pressure of the fission gas contained in the fuel elements increases and the gas escapes into the cell through the cracks in the defective fuel elements. However, this technique does not allow identification of the defective fuel elements to be replaced.

It has also been suggested to apply known techniques of non-destructive ultrasonic testing to inspection of fuel elements, before mounting in place in their assemblies, and to detection of defective fuel elements after irradiation. Many of these methods are applicable only to a separate fuel element while it is not immersed, which constitutes a troublesome limitation. Among these methods there may be mentioned heating of the expansion chamber followed by ultrasonic detection of water condensed on the cap (French Patent Applications Nos. 2 222 732 and 2 365 185) and measurement of the attenuation, caused by water which may be contained in the element, of an ultrasonic wave transmitted in the sheath (French Patent Applications Nos. 2 287 753 and 2 341 182). This line of thought in the prior art may be attributed to the fact that it has been attempted to preserve the measurement from the effect of the surrounding medium. However, there have also been suggested methods of detecting defective fuel elements while these are immersed. The methods suggested up to now only relate to detection of one indication representative of a fault, in particular the presence of water in the sheath. For example, it has been suggested to detect the presence of liquid water in the lower portion of each element in the expansion chamber, by directing an ultrasonic beam transversely to the element (French Patent Application No. 2 341 183). A preferred method (French Patent Application No. 2 493 025) consists of detecting the ultrasonic energy diffused in the liquid body by a fault present in an element in which the ultrasonic waves travel.

It is an object of the invention to improve upon the prior art methods for detecting defective fuel elements. It is a more specific object to provide a method which is responsive to various features indicative of a fault, particularly both to entry of water in the sheath and to the presence of cracks or flaws therein. For achieving that result, the inventors had to appreciate a number of factors which had been neglected or overlooked. The first is that ultrasonic waves having a frequency such that they travel in the "plate" mode or Lamb mode, already suggested for inspection of fuel elements which are new and not immersed (French Patent Application No. 2 454 675) are not appreciably attenuated by a liquid surrounding the outer surface of the sheath. A second discovery, also important, is that the simultaneous presence of pellets of fuel and a film of water surrounding them in the sheath causes a very large attenuation of the Lamb waves in the $S_o$ mode whereas it was known that there would be hardly any attenuation in a sheath containing no fuel, but containing water, even in a large amount.

A method according to the invention for detecting defective nuclear fuel elements in an assembly immersed in liquid using ultrasonic absorption includes the steps of transmission in the sheath, from an end part of the latter, of a signal comprising a train of ultrasonic waves having a frequency and duration chosen such that propagation takes place as Lamb waves, and detection of echoes; and repetition of transmission and reception at different frequencies, situated in a range of frequencies part of which corresponds to substantial absorption by water located in the sheath and part of which corresponds to a major formation of echo at a structural fault in the sheath.

To cause propagation in the Lamb mode in a sheath, the ultrasonic sound waves shall be applied in the form of a train, with a frequency such that the wavelength is equal to or less than the thickness of the sheath. The upper limit of the acceptable frequency range is therefore easily determined. Within the range thus defined, a first range of frequencies is selected which corresponds to maximum absorption responsive to presence of a film of water between the pellets and the sheath and a second range is selected which corresponds to detection of mechanical faults in the sheath. In practice, there is used for the detection of the presence of liquid a first range of frequencies $f_1$ less than the range of frequencies $f_2$ for detection of mechanical faults. The ranges $f_1$ and $f_2$ will correspond as a general rule to a frequency less than 1 megahertz, that is to say considerably less than the frequencies now used for ultrasonic inspection of metal articles.

In carrying out later an analysis of the return echoes of the trains of ultrasonic waves applied to the spring through the end cap, trains of a frequency and duration such that there is propagation in the Lamb mode of type $A_o$ or $A_1$ in the spring, there is obtained an indication of the gas pressure prevailing in the expansion chamber and surrounding the spring. The range of frequencies corresponding to the latter determination is generally considerably less than $f_1$ and $f_2$.

It is advantageous to carry out inspection of a rod in a single sequence of operations, by application of a single transducer, coupled to an end cap or to the sheath, used as a transmitter and also as a detector, for trains of waves of which the frequency is progressively varied to sweep the ranges $f_1$, $f_2$ and $f_3$. In each of these preselected ranges it is possible either to increase the maximum value of the echoes or, better, to take an average of the echoes over the whole of the preselected range. By sampling and digitisation, it is also possible to arrange the information from the tests and to apply to them any mathematical treatment intended to produce the useful information and to reduce the base noise.

The invention also relates to a device for detecting defective fuel elements in a nuclear feul assembly, each of the elements comprising an impervious sheath containing a stack of pellets of fuel surrounded by an atmosphere of gas under pressure, which device is characterized in that it comprises: an electro-acoustic transducer which can apply trains of ultrasonic waves in the Lamb mode to the sheath; a generator for exciting the transducer with trains of waves having different frequencies in ranges corresponding to propagation in the Lamb mode and, for one of the ranges, to considerable adsorption in the event of the presence of liquid in the sheath; and circuits for reception and treatment of the echoes.

It is possible, by calculation, using the usual criteria, for example those explained by Voktorov in "Rayleigh and Lamb waves", to determine approximately the ranges of frequency corresponding to propagation in the S mode (symmetric) and A mode (anti-symmetric) for a given thickness of sheath, dimension of spring and a given type of material. However, only experiment allows determination, for each rod, of the optimum frequency. As this frequency may vary from rod to rod because of tolerances of the latter, it suffices to use a range of frequencies covering the optimum values for the group of rods and to take for each of them, a mean of the echoes obtained at the different frequencies in the range.

The invention will be better understood from the following description and particular embodiments given by way of non-limiting example.

SHORT DESCRIPTION OF THE DRAWINGS

Figure 2:
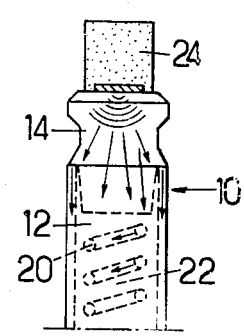
FIG. 2 shows the mounting of an axial transducer on the upper cap of an element of the type shown in FIG. 1.
Figure 9:
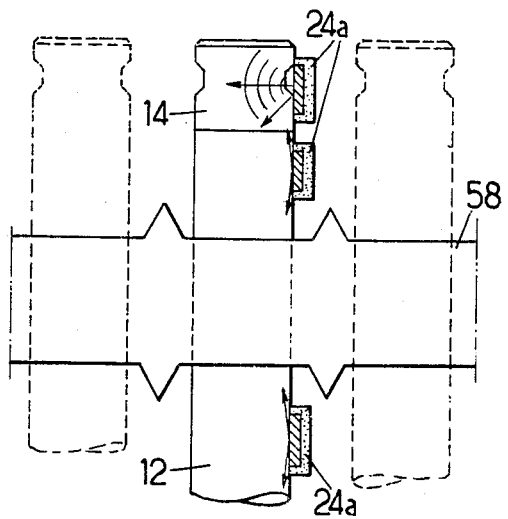
Figure 3A:
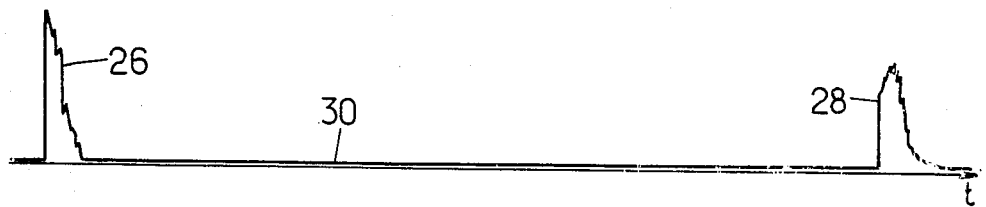
FIGS. 3A, 3B, 3C and 3D show the traces of signals which appear for different states of a fuel element, in the case of waves of mode $S_o$.
Figure 3B:
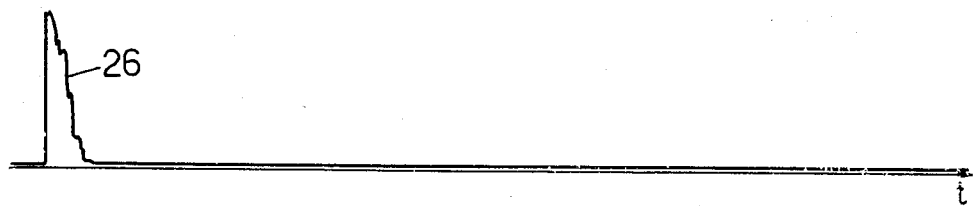
Figure 3C:
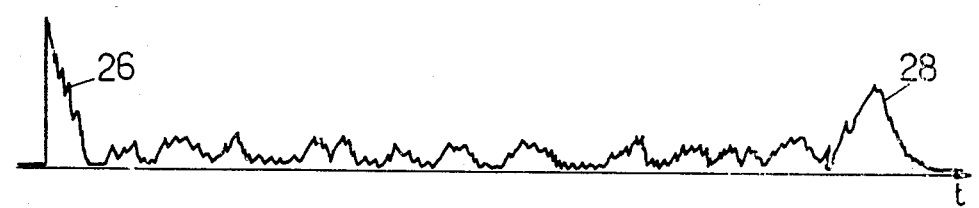
Figure 3D:
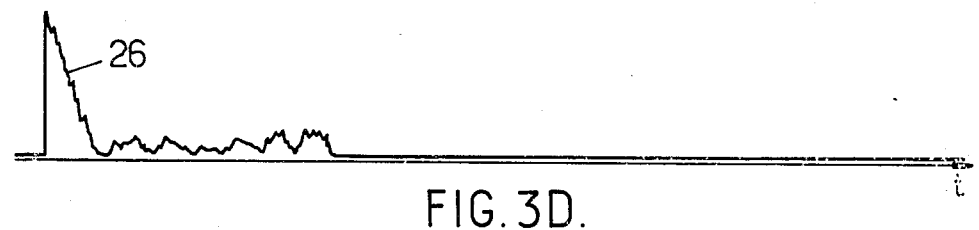
Figure 4:
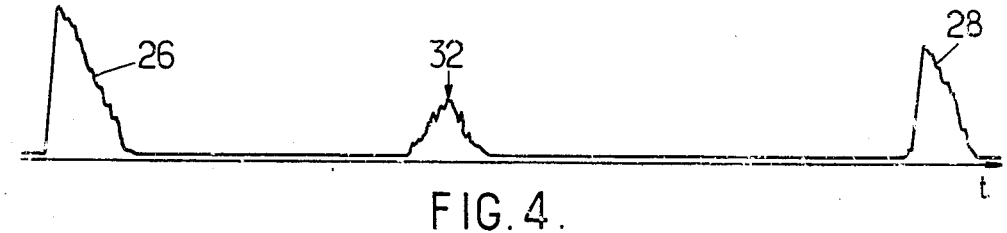
Figure 5A:
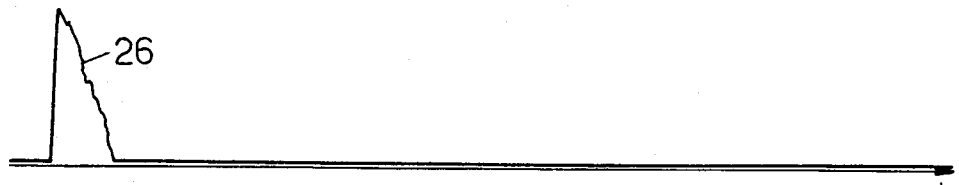
Figure 5B:
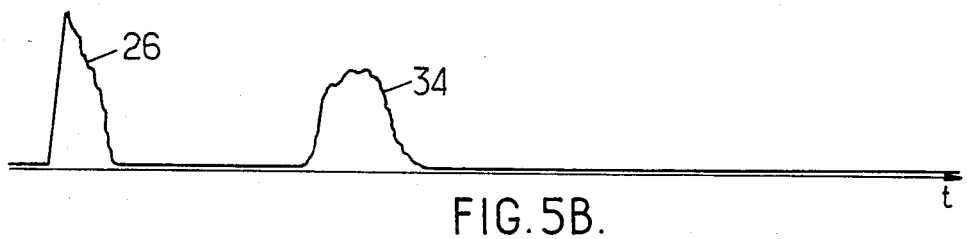
Figure 7:
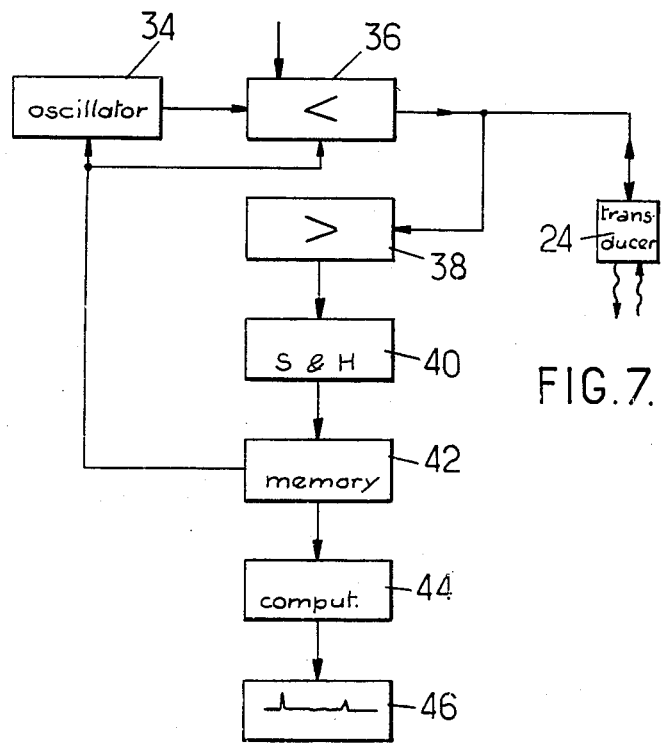
Figure 6:
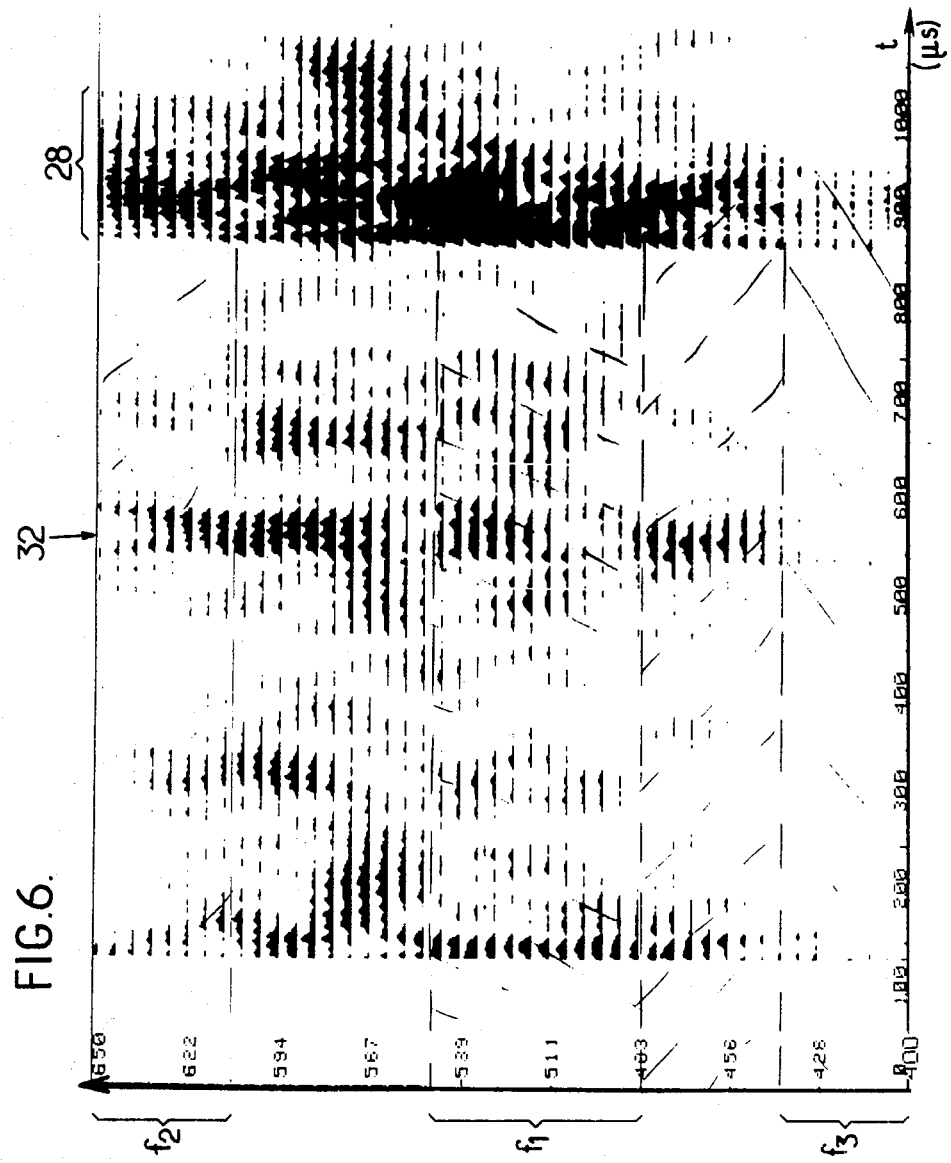
Figure 8:
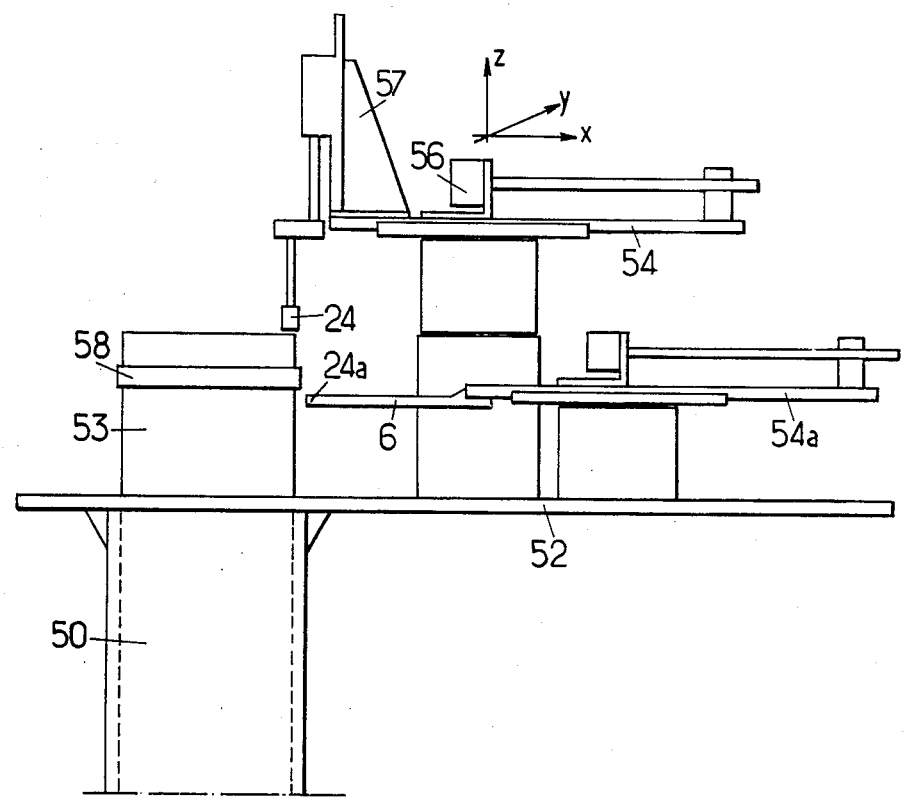
Figure 10:
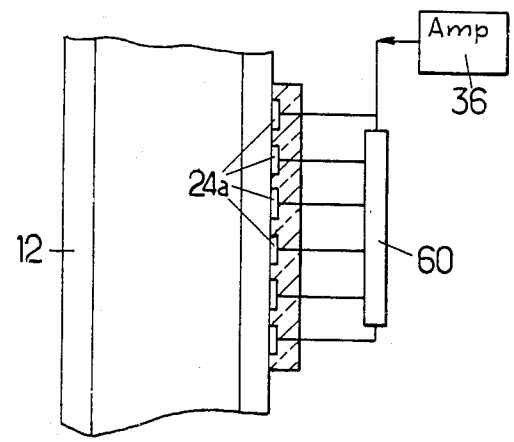
Figure 11:
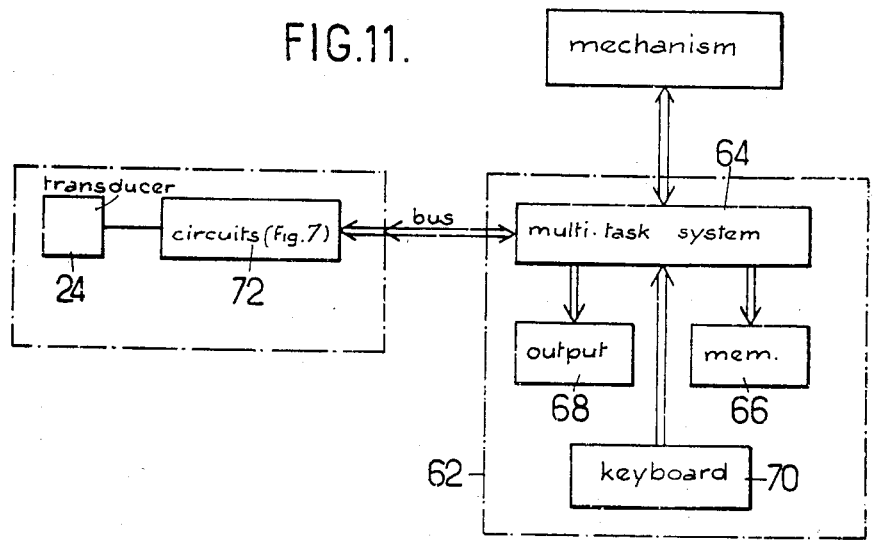

FIG. 4, similar to FIG. 3, shows the trace of a signal appearing in mode $S_o$ in case of a mechanical fault in the sheath;

FIGS. 5A and 5B show schematically the trace of signals appearing during exploration in modes $A_o$ and $A_1$;

FIG. 6 shows the echoes obtained during successive trails with scanning of the frequencies;

FIG. 7 is a block diagram of the electronics which may be associated with the transducer;

FIG. 8 shows schematically a mechanism which may be used for mounting in place the transducer of the device on successive elements in the same assembly;

FIG. 9, similar to FIG. 2, shows possible arrangements of a radial transducer;

FIG. 10 shows a possible mode of formation of several elements of a radial transducer;

FIG. 11 is a block diagram of a system for controlling the whole device.

DETAILED DESCRIPTION OF PREFERRED EMBODIMENTS

Before describing the invention itself, it may be useful to give a brief description of a fuel element to which it may be applied. This element 10, intended to be assembled with identical elements in a fuel assembly for a light-water reactor, comprises a sheath 12 which will frequently have a length of several meters. This sheath, generally of an alloy based on Zirconium, is closed imperviously by two welded end caps 14 and 16. The sheath 12 contains a stack of pellets 18 of nuclear fuel held in contact with the lower cap 16 by a spring 20 situated in an expansion chamber 22. Th cap 14 is provided with a hole 23 allowing purging of the fuel element 10 after assembly of its components to introduce helium under high pressure (typically about 30 bars) before obturation of the hole. The pellets 18 are given an initial diameter slightly smaller than the interior diameter of the sheath 12, so as to allow swelling of the pellets on irradiation. Consequently, a film of gas exists between the sheath and the major part of the periphery of each pellet 18.

When such a fuel element 10 is irradiated in a reactor, faults may appear, especially as cracking of the sheath. This cracking causes in turn a loss of pressure and, following cycling, entry of water inside the sheath. The invention allows detection of various indications of a fault.

For this purpose, the invention uses phenomena of absorption and reflection of ultrasonic waves applied to the elements 10, propagated in Lamb modes. FIG. 2 shows schematically an electro-acoustic transducer 24 coupled to plug 14 and capable of applying to it trains of ultrasonic waves of frequency and duration chosen so that propagation takes place in the Lamb mode. As will be seen below, the transducer may be placed radially.

Before describing the circuits which are required to be associated with it, the method of detection of the various indications of a fault will be defined.

Detection of presence of water in the sheath

Detection is carried out by applying, to the cap 14 in the case of FIG. 2, by means of transducer 24, trains of waves of frequency and duration corresponding to a So mode of Lamb waves and measuring the amplitude of the echoes caused by reflection on the lower cap 16. The transducer clearly has to be of a type allowing a wide range of operating frequencies and it is excited at successive frequencies which are regularly distributed, in a first range of frequencies $f_1$ chosen to correspond to a particularly marked zone of absorption by water which may be present in the sheaths. This range of frequencies $f_1$ having to correspond to propagation in the Lamb mode, its upper limit should not exceed a value which corresponds to a wavelength of the same order as the thickness of the wall. In practice, detection of the presence of water is carried out at a considerably lower range of frequencies.

In the case of an intact fuel element which does not contain water, in which the pellets are in contact with the sheath to only a small extent, the signal from the transducer 24 has the shape shown in FIG. 2A comprising an emission peak 26 and a high reception peak 28, caused by echo from the lower cap 16. Absorption by the sheath is low. On a trace obtained by taking the mean of the values obtained from several successive trials in the range of frequencies $f_1$, it is shown as a low base noise appearing at 30.

If on the other hand the element is defective and contains water, echo 28 disappears partially or totally (FIG. 2B) because of attenuation of the wave associated with the simultaneous presence of water and pellets 18. In practice, this attenuation is sufficiently large, in a typical element of several meters length, for complete disappearance of the echo 28.

In an intact element, but after irradiation has caused swelling of the pellets so that they are in contact with the sheath, there appears a relatively large base noise of the type shown in FIG. 3C. This alteration may be attributed to the presence of numerous points of contact and small agglomerates resulting from solid fission products. However this base noise does not at all interfere with detection of the presence of water, which shows itself not only by suppression of the echo 28 from the lower cap 16 but also by attenuation of the echoes obtained from contacts between pellets and the sheath in the wet zone of the rod (FIG. 3D).

Detection of mechanical faults in the sheath

Detection of mechanical faults in the sheath is carried out by measuring the echoes caused by these faults. This method is that which is currently used in non-destructive testing by ultrasonics, the time interval between emission and reception indicating the location of a fault. This detection will be carried out at a range of frequencies $f_2$ chosen to correspond to a mode of propagation $S_o$ and a reduced absorption by water which may be present in the sheath. This range $f_2$ will in general be chosen at the upper limit corresponding to propagation as Lamb waves. Whereas in the case of an intact rod there is obtained a response curve as shown in FIG. 3A, a rod having a crack or a hole will given an intermediate echo 30 (FIG. 4).

Detection of loss of pressure

Figure 1:
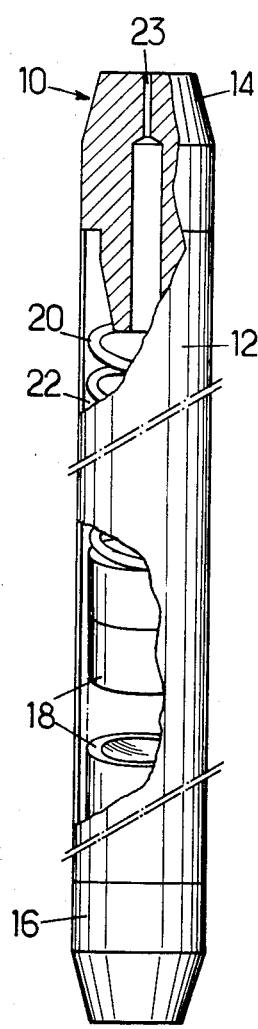
FIG. 1 is a schematic diagram, in elevation and partial section, of a fuel element of the type normally known as a "rod" to which the invention may be applied.

To detect faults of imperviosity in the sheath, which are shown as a loss of internal pressure, the transducer 24 is excited by a train of sinusoidal waves of long duration, at successive frequencies chosen in a range $f_3$ such that the ultrasonic sound is propagated in the spring 20 (FIG. 1) according to the modes of Lamb waves $A_o$ and/or $A_1$. These modes have the characteristic of showing an attenuation which is very sensitive to the environment of the medium in which they are propagated, that is to say the atmosphere surrounding the spring 20. When the sheath interior is at a normal pressure of 30 bars, there is total attenuation of modes $A_o$ and $A_1$, producing the signal shown in FIG. 5A. When on the other hand the gas contained in the expansion chamber has escaped and the pressure has fallen to a value close to atmospheric, there is detected a large echo 34 on the end of the spring (FIG. 5B).

Testing is advantageously carried out by successive trials sweeping the frequency spectrum, which generates a series of echoes such as those shown schematically in FIG. 6.

This FIG. 6 shows echo detections corresponding to successive trials at frequencies separated by 5.55 KHz, from 400 to 650 KHz. In a first range of frequencies $f_3$, the transducer is excited so as to generate ultrasonic sound in modes $A_o$ and $A_1$ in the spring. The absence of an echo at a distance corresponding to the end of the spring shows that pressurization is maintained. In the range $f_1$, extending from about 403 to 550 KHz, there is found considerable base noise, showing swelling of the pellets, and the presence of echoes 28 on the various surfaces of the lower end cap, indicating the absence of water. Finally, in the range of frequencies $f_2$ there appears at 32 an echo showing a mechanical fault. This echo also appears in the range of frequencies $f_1$, but drowned in the heavy base noise which has almost completely disappeared in range $f_2$.

The electronics associated with transducer 24 may have the structure shown in FIG. 7 and comprise a generator of sinusoidal waves 34 at variable and controlled frequency. This generator feeds an emission amplifier 36 which allows provision of a train of waves at given duration or number of wavelengths. The output of this emission amplifier 36 is connected to transducer 24. The reflected waves received by the transducer are sent, directly or through a separator, to a receiver amplifier 38. The echo signals received by the amplifier 38 are processed numerically. For this purpose, the output of amplifier 38 is fed to a sampler 40 of which the output samples are fed to a storage memory 42. After sampling for a duration corresponding to the return journey of the ultrasonic wave between the transducer 24 and the end cap, the storage memory gives the generator 34 a circuit for increase of frequency and, to the amplifier 36, an actuation signal causing emission of a further train. An arithmetic circuit 44 associated with the memory 42 allows calculation of the mean of the echoes for all the trials and display on the visual system 46. Sweeping at the frequency over a whole range, associated with a calculation of the mean which may be carried out by a microprocessor, enables allowance to be made for variations between fuel elements, due especially to tolerances in manufacture (anisotropy of materials, variation in the welds etc.).

The mounting in place of the device on each rod in turn is carried out by a mechanism controlled from a distance which may be constructed as shown schematically in FIG. 8 when the transducer 24 is intended to be placed axially on the cap. The mechanism comprises an arm 52 integral with a housing 50 for receiving the fuel assembly 53 comprising the elements to be inspected. The mechanism comprises a table 54 movable along x and y co-ordinate axes, only the motor 56 for displacement along x being shown. This table carries a bracket 57 provided in turn with means for displacing the transducer 24 along the z axis, that is parallel to the direction of the elements. The vertical movement of this means is sufficient to allow introduction of the transducer between the guide tubes which extend beyond the fuel elements once the upper end piece of the assembly 53 has been removed.

Instead of using a transducer 24 arranged axially on the cap of the element, it is possible to use a radial transducer 24a (FIG. 9). The transducer, arranged to emit a beam of ultrasonic sound perpendicular to a generatrix of the sheath 12, may be placed at different heights. In a known type of assembly for a pressurized water reactor, comprising an upper spacer grid 58, it may be placed at the height of the upper cap 14, immediately above the grid 58 or immediately below, so as to remain in all cases at the level of the chamber 22. In this case the most advantageous position is generally just below the spacer grid 58, which allows variations in positioning due to irradiation to be accounted for. In an embodiment of radial transducer 24a the latter is formed of several elements connected to the same amplifier 36 through successive tappings on a delay line 60, the tappings corresponding to delays equal to the time of propagation from one emitter to the next. The wave generated in the sheath 12 is formed of the resultant of the waves emitted by each of the elements forming the transducer and it is analogous to that which would generate an oblique wave front arriving at the sheath (FIG. 10).

The mechanism for mounting in place a radial transducer 24a may be very similar to that for mounting in place an axial transducer, but it is not necessary to provide movement in the z direction. FIG. 8 also shows such a simplified mechanism, again comprising a table 54a displaceable in co-ordinate directions, of which the level is adjusted such that the transducer 24a passes just below the upper grid 58. Such a transducer is applicable to all assemblies in which the rods are provided with at least one expansion chamber 22.

Whatever the mechanism used, it is advantageously associated with an information system which also ensures operation of the electronics of FIG. 7. This information system 62 may use the principle of construction shown in FIG. 11 and be composed of a multi-functional system 64 associated with an information storage memory 66, an all-or-nothing information output terminal 68 and a central keyboard 70. The multi-function system is coupled by a bus to the electronics 72 of which the detail is shown in FIG. 7, which is connected to the transducer 24.

The multi-function system 64 is also provided to operate the system and, in particular, carry out automatically mounting in place of the transducer 24 on each element in turn. In the case of an axial transducer, the procedure for mounting in place may be as follows: the probe being in an elevated position and approximately in line with an element 10 to be inspected, echoes reflected from the cap 14 are received first on sweeping along x, then on sweeping along y. The amplitude of the reflected echo from the cap passes through a maximum in each of these directions and coincidence of the two maxima indicates exact positioning on the axis of the rod. Once this position has been determined, the system 64 controls movement along z up to contact.

It will be seen that this mounting in place takes place in real time without recording or delayed analysis or repositioning. It allows compensation for faults in position of rods with respect to their theoretical positions and deteriorations due to irradiation.

I claim:

1. A method for detecting defects in nuclear fuel elements of the type having a fluid tight sheath and a stack of nuclear fuel pellets in said sheath separated by a plenum chamber from an end plug closing an end of said sheath, comprising the steps of: (a) maintaining said fuel elements immersed in a body of liquid; (b) applying to the sheath, through said end plug, a train of ultrasonic waves having a frequency and duration such that propagation takes place as Lamb waves; (c) detecting echoes of said train; (d) repeating steps (b) and (c) for different frequencies, some of them are in the range of frequencies which corresponds to substantial absorption by water which may be contained in the sheath and others of them are in a second range which corresponds to formation of an echo at a mechanical fault in the sheath.

2. A method according to claim 1, wherein said first one of said ranges of frequency is selected to correspond to maximum absorption of ultrasonic energy by a film of water present between said pellets and said sheath and said second one of said ranges corresponds to formation of echoes by mechanical faults in the sheath.

3. A method according to claim 1 for detection of defective nuclear fuel elements among fuel elements of the type comprising a spring placed in said plenum chamber between said end plug and said stack, comprising the additional steps of applying to the spring a train of ultrasonic sound pulses of frequency and duration such that propagation takes place as Lamb waves in the $A_o$ or $A_1$ mode, and detecting echoes from the end of the spring.

4. A method according to claim 1, wherein transmission and detection are repeated at a plurality of different frequencies in each said range.

5. A method according to claim 1 wherein the measurements obtained at a plurality of different frequencies in each said range are averaged.

6. A device for detecting defective fuel elements in a nuclear fuel assembly having a plurality of said fuel elements each of which comprises an elongated sheath which contains a stack of fuel pellets in an atmosphere of gas under pressure and is closed by an end plug, comprising an electro-acoustic transducer arranged for location on said end plug and for applying trains of ultrasonic waves in the Lamb mode to the sheath through said end plug, a generator capable of energizing the transducer by trains of waves having different frequencies in a plurality of ranges corresponding to propagation in the Lamb mode, one of said ranges corresponding to absorption in the event of presence of liquid in the sheath, and electronic receiving and processing circuits for measuring echoes received by said transducer.

7. A device according to claim 6, further comprising a mechanism for placing said transducer on the end plug of each one of said fuel elements.

8. A device according to claim 6, further comprising a mechanism for placing the transducer, which is of a radial type, on the lateral surface of the element at a longitudinal position where it confronts the plenum chamber.

* * * * *

UNITED STATES PATENT AND TRADEMARK OFFICE
CERTIFICATE OF CORRECTION

PATENT NO. : 4,684,493

DATED : August 4, 1987

INVENTOR(S) : Alain Gravelle

It is certified that error appears in the above-identified patent and that said Letters Patent is hereby corrected as shown below:

On the title page, insert:

-- [30] Foreign Application Priority Data

Dec. 17, 1982   France [FR].....8221243 --.

Signed and Sealed this

Fourteenth Day of March, 1989

*Attest:*

DONALD J. QUIGG

*Attesting Officer*    *Commissioner of Patents and Trademarks*